(12) United States Patent
Grajcar et al.

(10) Patent No.: US 10,206,378 B2
(45) Date of Patent: Feb. 19, 2019

(54) SYSTEM AND METHOD OF ENHANCING SWINE REPRODUCTION

(71) Applicant: Once Innovations, Inc., Plymouth, MN (US)

(72) Inventors: Zdenko Grajcar, Orono, MN (US); Juliette Delabbio, Natchitoches, LA (US)

(73) Assignee: Once Innovations, Inc., Plymouth, MN (US)

( * ) Notice: Subject to any disclaimer, the term of this patent is extended or adjusted under 35 U.S.C. 154(b) by 0 days.

(21) Appl. No.: 15/108,690

(22) PCT Filed: Jan. 7, 2015

(86) PCT No.: PCT/US2015/010407
§ 371 (c)(1),
(2) Date: Jun. 28, 2016

(87) PCT Pub. No.: WO2015/105823
PCT Pub. Date: Jul. 16, 2015

(65) Prior Publication Data
US 2016/0316727 A1 Nov. 3, 2016

Related U.S. Application Data

(60) Provisional application No. 61/924,477, filed on Jan. 7, 2014.

(51) Int. Cl.
| *A01K 67/02* | (2006.01) |
|---|---|
| *A01K 29/00* | (2006.01) |
| *A01K 1/02* | (2006.01) |

(52) U.S. Cl.
CPC ................ *A01K 67/02* (2013.01); *A01K 1/02* (2013.01)

(58) Field of Classification Search
CPC ... A01L 29/00; A01K 2227/108; A01K 67/02; A01K 1/02
(Continued)

(56) References Cited

U.S. PATENT DOCUMENTS

| 4,239,020 A | 12/1980 | Kiyokawa et al. |
| 4,271,788 A | 6/1981 | Knowles |

(Continued)

FOREIGN PATENT DOCUMENTS

| CH | 662244 A5 | 9/1987 |
| CN | 101162847 A | 4/2008 |

(Continued)

OTHER PUBLICATIONS

"International Application Serial No. PCT/US2015/010407, International Search Report dated Apr. 7, 2015", 2 pgs.

(Continued)

*Primary Examiner* — Yvonne R Abbott-Lewis
(74) *Attorney, Agent, or Firm* — Schwegman Lundberg & Woessner, P.A.

(57) ABSTRACT

A method of increasing the probability of breeding swine via a lighting system with a programmable timing device. The lighting system is programmed to present differing photoperiods such that the amount of light observed by a swine every day or week gradually decreases, mimicking a seasonal change, typically from summer to fall. As a result, swine psychologically and physiologically believe that seasons are changing resulting in increased probability of breeding for the swine.

12 Claims, 6 Drawing Sheets

(58) Field of Classification Search
USPC .................................................. 119/720, 174
See application file for complete search history.

(56) References Cited

U.S. PATENT DOCUMENTS

| | | | |
|---|---|---|---|
| 4,625,728 A | 12/1986 | Schonberg | |
| 4,700,887 A | 10/1987 | Timmons | |
| 4,721,062 A | 1/1988 | Williams et al. | |
| 4,872,421 A | 10/1989 | Laurent et al. | |
| 4,939,426 A | 7/1990 | Menard et al. | |
| 33,600 A | 6/1991 | Timmons | |
| 5,036,797 A | 8/1991 | Koozer | |
| 5,108,907 A | 4/1992 | Pleass | |
| 5,188,907 A | 2/1993 | Kawahara et al. | |
| 5,482,210 A | 1/1996 | Carey et al. | |
| 5,495,147 A | 2/1996 | Lanzisera | |
| 5,575,459 A | 11/1996 | Anderson | |
| 5,602,709 A | 2/1997 | Al-Dabbagh | |
| 5,900,929 A | 5/1999 | Hebrank et al. | |
| 6,016,038 A | 1/2000 | Mueller et al. | |
| 6,166,496 A | 12/2000 | Lys et al. | |
| 6,224,243 B1 | 5/2001 | Karton | |
| 6,236,622 B1 | 5/2001 | Blackman | |
| 6,252,254 B1 | 6/2001 | Soules et al. | |
| 6,357,889 B1 | 3/2002 | Duggal et al. | |
| 6,461,019 B1 | 10/2002 | Allen | |
| 6,573,254 B1 | 6/2003 | Kuenzel et al. | |
| 6,636,003 B2 | 10/2003 | Rahm et al. | |
| 6,766,767 B2* | 7/2004 | El Halawani .......... | A01K 45/00 119/174 |
| 6,789,500 B2 | 9/2004 | Rozenboim | |
| 6,810,832 B2 | 11/2004 | Ford | |
| 6,933,707 B2 | 8/2005 | Allen | |
| 6,953,266 B1 | 10/2005 | Ver Hage et al. | |
| 7,038,399 B2 | 5/2006 | Lys et al. | |
| 7,081,722 B1 | 7/2006 | Huynh et al. | |
| 7,102,334 B2 | 9/2006 | Wiegand et al. | |
| 7,102,344 B1 | 9/2006 | Short et al. | |
| 7,131,397 B2 | 11/2006 | El Halawani et al. | |
| 7,213,942 B2 | 5/2007 | Jiang et al. | |
| 7,220,018 B2 | 5/2007 | Crabb et al. | |
| 7,288,902 B1 | 10/2007 | Melanson | |
| 7,352,138 B2 | 4/2008 | Lys et al. | |
| 7,358,679 B2 | 4/2008 | Lys et al. | |
| 7,378,805 B2 | 5/2008 | Oh et al. | |
| 7,391,630 B2 | 6/2008 | Acatrnei | |
| 7,425,801 B2 | 9/2008 | Ozaki | |
| 7,436,134 B2 | 10/2008 | Levine | |
| 7,489,086 B2 | 2/2009 | Miskin et al. | |
| 7,709,774 B2 | 5/2010 | Schulz et al. | |
| 7,723,926 B2 | 5/2010 | Mednik et al. | |
| 7,781,979 B2 | 8/2010 | Lys | |
| 7,791,289 B2 | 9/2010 | Oosterbaan et al. | |
| 7,847,486 B2 | 12/2010 | Ng | |
| 7,859,196 B2 | 12/2010 | Lee et al. | |
| 7,863,831 B2 | 1/2011 | Vos | |
| 7,880,400 B2 | 2/2011 | Zhou et al. | |
| 7,902,769 B2 | 3/2011 | Shteynberg et al. | |
| 7,936,135 B2 | 5/2011 | Hum et al. | |
| 7,977,892 B2 | 7/2011 | Lee et al. | |
| 8,102,167 B2 | 1/2012 | Irissou et al. | |
| 8,120,279 B2 | 2/2012 | Oosterbaan et al. | |
| 8,134,303 B2 | 3/2012 | Lys | |
| 8,159,125 B2 | 4/2012 | Miao | |
| 8,164,276 B2 | 4/2012 | Kuwabara | |
| 8,188,679 B2 | 5/2012 | Hoogzaad | |
| 8,188,687 B2 | 5/2012 | Lee et al. | |
| 2,465,329 A1 | 6/2012 | Zdenko | |
| 8,205,577 B2 | 6/2012 | Sia et al. | |
| 8,324,642 B2 | 12/2012 | Grajcar | |
| 8,324,840 B2 | 12/2012 | Shteynberg et al. | |
| 8,373,363 B2 | 2/2013 | Grajcar | |
| 8,384,307 B2 | 2/2013 | Grajcar | |
| 8,468,976 B2 | 6/2013 | Kakimi et al. | |
| 8,531,136 B2 | 9/2013 | Grajcar | |
| 8,593,044 B2 | 11/2013 | Grajcar | |
| 8,596,804 B2 | 12/2013 | Grajcar | |
| 8,598,799 B2 | 12/2013 | Tai et al. | |
| 8,643,308 B2* | 2/2014 | Grajcar .............. | H05B 33/0809 315/185 R |
| 8,657,463 B2 | 2/2014 | Lichten et al. | |
| 8,773,031 B2 | 7/2014 | Sadwick et al. | |
| 8,796,955 B2 | 8/2014 | Grajcar | |
| 8,858,005 B2 | 10/2014 | Grajcar | |
| 8,922,136 B2 | 12/2014 | Grajcar | |
| 9,155,151 B2 | 10/2015 | Angeles | |
| 9,210,755 B2 | 12/2015 | Grajcar | |
| 9,247,603 B2 | 1/2016 | Grajcar et al. | |
| 9,433,046 B2 | 8/2016 | Grajcar | |
| 9,700,019 B2 | 7/2017 | Grajcar et al. | |
| 9,709,228 B2 | 7/2017 | Grajcar | |
| 9,844,210 B2 | 12/2017 | Grajcar et al. | |
| 2002/0003233 A1 | 1/2002 | Mueller-Mach et al. | |
| 2002/0047606 A1 | 4/2002 | Guthrie et al. | |
| 2002/0097007 A1 | 7/2002 | Koncz et al. | |
| 2002/0149929 A1 | 10/2002 | Evans et al. | |
| 2003/0164809 A1 | 9/2003 | Leung | |
| 2003/0172878 A1 | 9/2003 | Halawani et al. | |
| 2005/0212458 A1 | 9/2005 | Powers, Jr. et al. | |
| 2005/0241593 A1 | 11/2005 | Kaura | |
| 2005/0256554 A1 | 11/2005 | Malak | |
| 2005/0276720 A1 | 12/2005 | Correa | |
| 2005/0280964 A1 | 12/2005 | Richmond et al. | |
| 2007/0086912 A1 | 4/2007 | Dowling et al. | |
| 2007/0182338 A1 | 8/2007 | Shteynberg et al. | |
| 2007/0258240 A1 | 11/2007 | Ducharme et al. | |
| 2008/0012722 A1 | 1/2008 | Moseley et al. | |
| 2008/0017120 A1 | 1/2008 | Hawk | |
| 2008/0116816 A1 | 5/2008 | Neuman et al. | |
| 2008/0174233 A1 | 7/2008 | Bawendi et al. | |
| 2008/0178819 A1 | 7/2008 | Sia et al. | |
| 2008/0198009 A1 | 8/2008 | Hoeben et al. | |
| 2008/0202443 A1 | 8/2008 | Potter | |
| 2008/0203936 A1 | 8/2008 | Mariyama et al. | |
| 2008/0211421 A1 | 9/2008 | Lee et al. | |
| 2008/0218995 A1 | 9/2008 | Gilkey et al. | |
| 2009/0096739 A1 | 4/2009 | Lan et al. | |
| 2009/0160370 A1 | 6/2009 | Tai et al. | |
| 2009/0185373 A1 | 7/2009 | Grajcar | |
| 2009/0267534 A1 | 10/2009 | Godbole et al. | |
| 2010/0013402 A1 | 1/2010 | Chaffai et al. | |
| 2010/0060175 A1 | 3/2010 | Lethellier | |
| 2010/0072903 A1 | 3/2010 | Blaut et al. | |
| 2010/0164579 A1 | 7/2010 | Acatrinei | |
| 2010/0165677 A1 | 7/2010 | Wang et al. | |
| 2010/0237800 A1 | 9/2010 | Kang et al. | |
| 2010/0294205 A1* | 11/2010 | Kakimi ................ | A01K 31/18 119/437 |
| 2010/0308739 A1 | 12/2010 | Shteynberg et al. | |
| 2010/0308751 A1 | 12/2010 | Nerone | |
| 2010/0310552 A1 | 12/2010 | Rapp et al. | |
| 2011/0018465 A1 | 1/2011 | Ashdown | |
| 2011/0031888 A1 | 2/2011 | Datta et al. | |
| 2011/0031890 A1 | 2/2011 | Stack et al. | |
| 2011/0037415 A1 | 2/2011 | Juestel et al. | |
| 2011/0084619 A1 | 4/2011 | Gray | |
| 2011/0101883 A1* | 5/2011 | Grajcar ................ | A01K 29/00 315/291 |
| 2011/0210678 A1 | 9/2011 | Grajcar | |
| 2011/0228515 A1 | 9/2011 | Grajcar | |
| 2011/0273103 A1 | 11/2011 | Hong | |
| 2012/0002408 A1* | 1/2012 | Lichten ................ | F21S 8/063 362/218 |
| 2012/0025709 A1 | 2/2012 | Zampini et al. | |
| 2012/0081009 A1 | 4/2012 | Shteynberg et al. | |
| 2012/0153833 A1 | 6/2012 | Mikani et al. | |
| 2012/0186524 A1 | 7/2012 | Grajcar | |
| 2012/0200229 A1 | 8/2012 | Kunst et al. | |
| 2012/0268918 A1 | 10/2012 | Grajcar | |
| 2012/0299500 A1 | 11/2012 | Sadwick et al. | |
| 2013/0016506 A1* | 1/2013 | Odom, Jr. ............ | A01K 31/18 362/231 |
| 2013/0069546 A1 | 3/2013 | Lin et al. | |
| 2013/0134888 A1 | 5/2013 | Grajcar | |

(56) References Cited

U.S. PATENT DOCUMENTS

| | | |
|---|---|---|
| 2013/0153938 A1 | 6/2013 | Grajcar |
| 2013/0157394 A1 | 6/2013 | Gr |
| 2013/0193864 A1 | 8/2013 | Angeles |
| 2013/0200812 A1 | 8/2013 | Radermacher et al. |
| 2013/0207555 A1 | 8/2013 | Qiu et al. |
| 2013/0342120 A1 | 12/2013 | Creusen et al. |
| 2014/0098531 A1 | 4/2014 | Grajcar |
| 2014/0103823 A1 | 4/2014 | Kahlman et al. |
| 2014/0111091 A1 | 4/2014 | Grajcar et al. |
| 2014/0159584 A1 | 6/2014 | Grajcar |
| 2014/0197741 A1 | 7/2014 | Sakai et al. |
| 2014/0197751 A1 | 7/2014 | Grajcar |
| 2014/0210352 A1 | 7/2014 | Grajcar |
| 2014/0210357 A1 | 7/2014 | Yan et al. |
| 2014/0252340 A1 | 9/2014 | Wang |
| 2015/0061534 A1 | 3/2015 | Grajcar |
| 2015/0069932 A1 | 3/2015 | Grajcar |
| 2015/0136037 A1 | 5/2015 | Boonekamp et al. |
| 2015/0230309 A1 | 8/2015 | Grajcar et al. |
| 2015/0247631 A1 | 9/2015 | Grajcar et al. |
| 2015/0273235 A1 | 10/2015 | Grajcar |
| 2016/0165698 A1 | 6/2016 | Grajcar |
| 2016/0212817 A1 | 7/2016 | Grajcar et al. |
| 2017/0273281 A1 | 9/2017 | Grajcar et al. |
| 2017/0290124 A1 | 10/2017 | Grajcar |

FOREIGN PATENT DOCUMENTS

| | | | |
|---|---|---|---|
| CN | 101672839 | A | 3/2010 |
| CN | 102612791 | A | 7/2012 |
| CN | 104106122 | A | 10/2014 |
| EP | 0064175 | A1 | 11/1982 |
| EP | 0229583 | A2 | 7/1987 |
| EP | 1502483 | A1 | 2/2005 |
| EP | 2094063 | A1 | 8/2009 |
| EP | 2465174 | A1 | 2/2011 |
| EP | 2666220 | A2 | 7/2012 |
| EP | 2795654 | A1 | 10/2014 |
| JP | H05199823 | A | 8/1993 |
| JP | 2004248333 | A | 9/2004 |
| JP | 2005137238 | A | 6/2005 |
| JP | 2006147933 | A | 6/2006 |
| JP | 2006244848 | A | 9/2006 |
| JP | 2007511903 | A | 5/2007 |
| JP | 2007299788 | A | 11/2007 |
| JP | 2008059811 | A | 3/2008 |
| JP | 2008218043 | A | 9/2008 |
| JP | 2009026544 | A | 2/2009 |
| JP | 2009035673 | A | 2/2009 |
| JP | 2009060069 | A | 3/2009 |
| JP | 2009117036 | A | 5/2009 |
| JP | 2009123427 | A | 6/2009 |
| JP | 2009171866 | A | 6/2009 |
| JP | 2011040701 | A | 2/2011 |
| JP | 2014516452 | A | 7/2014 |
| JP | 5676611 | B2 | 1/2015 |
| WO | WO-1984000693 | A1 | 3/1984 |
| WO | WO-0106630 | A1 | 1/2001 |
| WO | WO-02061427 | A1 | 8/2002 |
| WO | WO-2005084080 | A2 | 9/2005 |
| WO | WO-2008114250 | A1 | 9/2008 |
| WO | WO-2013044916 | A1 | 4/2013 |
| WO | WO-2014047473 | A1 | 3/2014 |
| WO | WO-2014052897 | A1 | 4/2014 |
| WO | WO-2014200960 | A1 | 12/2014 |
| WO | WO-2015002665 | A1 | 1/2015 |
| WO | WO-2015017655 | A1 | 2/2015 |
| WO | WO-2015105776 | A1 | 7/2015 |
| WO | WO-2015105823 | A1 | 7/2015 |
| WO | WO-2016033002 | A1 | 3/2016 |
| WO | WO-2017004318 | A1 | 1/2017 |
| WO | WO-2017172869 | A1 | 10/2017 |

OTHER PUBLICATIONS

"International Application Serial No. PCT/US2015/010407, Written Opinion dated Apr. 7, 2015", 4 pgs.

Taylor, Nina, "Lighting for Pig Units", Report compiled for BPEX, [Online]. Retrieved from the Internet: <http://www.bpex.org.uk/media/39814/lighting-for-pig-units-final-report.pdf>, (Apr. 30, 2010), 1-74.

"U.S. Appl. No. 14/906,685, Notice of Allowance dated Jul. 13, 2018", 5 pgs.

"European Application No. EP10827580.1 Extended European_Search_Report_dated Feb. 5, 2016", (dated Feb. 5, 2016), 6 pgs.

"European Application No. EP10827580.1 Office Action_dated Apr. 13, 2017", (dated Apr. 13, 2017), 5 pgs.

"European Application No. EP11757037.4 European_Search_Report_dated Nov. 24, 2017", (dated Nov. 24, 2017), 9 pgs.

"European Application No. EP12739301.5 European_Search_Report_dated Nov. 24, 2017", (dated Nov. 24, 2017), 10 pgs.

"European Application No. EP15735446.5 European_Search_Report_dated Jul. 26, 2017", (dated Jul. 26, 2017), 9 pgs.

"Global Dossier Translation of 1st Office Action dated Apr. 24, 2017 for CN Application No. CN201480047295.6", (dated Apr. 24, 2017), 9 pgs.

"Global Dossier Translation of 1st Office Action dated Jan. 26, 2014 for CN Application No. CN201080046791.1", (dated Jan. 26, 2014), 10 pgs.

"Global Dossier Translation of 1st Office Action dated Jan. 26, 2014 for CN Application No. CN201080046880.6", (dated Jan. 26, 2014), 7 pgs.

"Global Dossier Translation of 1st Office Action dated Jul. 2, 2014 for CN Application No. CN201180022574.3", (dated Jul. 2, 2014), 5 pgs.

"Global Dossier Translation of 1st Office Action dated Mar. 2, 2016 for CN Application No. CN2013800546160", (dated Mar. 2, 2016), 9 pgs.

"Global Dossier Translation of 1st Office Action dated May 27, 2014 for CN Application No. CN201280007111.4", (dated May 27, 2014), 12 pgs.

"Global Dossier Translation of 1st Office Action dated Oct. 25, 2016 for CN Application No. CN201510072474.1", (dated Oct. 25, 2016), 4 pgs.

"Global Dossier Translation of 1st Office Action dated Oct. 9, 2016 for CN Application No. CN201510214363.X", (dated Oct. 9, 2016), 7 pgs.

"Global Dossier Translation of 2nd Office Action dated Aug. 19, 2014 for CN Application No. CN201080046791.1", (dated Aug. 19, 2014), 5 pgs.

"Global Dossier Translation of 2nd Office Action dated Dec. 12, 2016 for CN Application No. CN201510072474.1", (dated Dec. 12, 2016), 4 pgs.

"Global Dossier Translation of 2nd Office Action dated Dec. 17, 2014 for CN Application No. CN201280007111.4", (dated Dec. 17, 2014), 13 pgs.

"Global Dossier Translation of 2nd Office Action dated Feb. 9, 2015 for CN Application No. CN201180022574.3", (dated Feb. 9, 2015), 7 pgs.

"Global Dossier Translation of 2nd Office Action dated May 12, 2017 for CN Application No. CN201510214363.X", (dated May 12, 2017), 6 pgs.

"Global Dossier Translation of 2nd Office Action dated Nov. 30, 2016 for CN Application No. CN2013800546160", (dated Nov. 30, 2016), 10 pgs.

"Global Dossier Translation of 2nd Office Action dated Sep. 26, 2017 for CN Application No. CN201480047295.6", (dated Sep. 26, 2017), 7 pgs.

"Global Dossier Translation of 3rd Office Action dated Aug. 27, 2015 for CN Application No. CN201180022574.3", (dated Jun. 7, 2018), 8 pgs.

"Global Dossier Translation of 3rd Office Action dated Feb. 5 2018 for CN Application No. CN201480047295.6", (dated Feb. 5, 2018), 6 pgs.

"Global Dossier Translation of 3rd Office Action dated Jun. 11, 2015 for CN Application No. CN201280007111.4", (dated Jun. 11, 2015), 5 pgs.

(56) References Cited

OTHER PUBLICATIONS

"Global Dossier Translation of 3rd Office Action dated Jun. 26, 2017 for CN Application No. CN2013800546160", (dated Jun. 26, 2017), 4 pgs.
"Global Dossier Translation of 3rd Office Action dated Oct. 19, 2017 for CN Application No. CN201510214363.X", (dated Oct. 19, 2017), 8 pgs.
"Global Dossier Translation of 4th Office Action dated Apr. 18, 2016 for CN Application No. CN201180022574.3", (dated Apr. 18, 2016), 4 pgs.
"Global Dossier Translation of 4th Office Action dated Nov. 25, 2015 for CN Application No. CN201280007111.4", (dated Nov. 25, 2015), 4 pgs.
"Hazards of Harmonics and Neutral Overloads", White Paper #26 APC Legendary Reliability, (2003), 8 pgs.
"International Application Serial No. PCT/US2010/045467, International Preliminary Report on Patentability dated Feb. 14, 2012", (dated Feb. 14, 2012), 7 pgs.
"International Application Serial No. PCT/US2010/045467, International Search Report dated Feb. 17, 2011", (dated Feb. 17, 2011), 2 pgs.
"International Application Serial No. PCT/US2010/045467, Written Opinion dated Feb. 14, 2012", (dated Feb. 14, 2012), 6 pgs.
"International Application Serial No. PCT/US2010/054506, International Preliminary Report on Patentability dated May 1, 2012", (dated May 1, 2012), 7 pgs.
"International Application Serial No. PCT/US2010/054506, International Search Report dated May 5, 2011", (dated May 5, 2018), 2 pgs.
"International Application Serial No. PCT/US2010/054506, Written Opinion dated Apr. 28, 2012", (dated Apr. 28, 2012), 6 pgs.
"International Application Serial No. PCT/US2010/054869, International Preliminary Report on Patentability dated May 1, 2012", (dated May 1, 2012), 5 pgs.
"International Application Serial No. PCT/US2010/054869, International Search Report dated May 5, 2011", (dated May 5, 2011), 2 pgs.
"International Application Serial No. PCT/US2010/054869, Written Opinion dated Apr. 29, 2012", (dated Apr. 29, 2012), 4 pgs.
"International Application Serial No. PCT/US2011/028910, International Preliminary Report on Patentability dated Sep. 18, 2012", (dated Sep. 18, 2012), 5 pgs.
"International Application Serial No. PCT/US2011/028910, International Search Report dated May 26, 2011", (dated May 26, 2011), 2 pgs.
"International Application Serial No. PCT/US2011/028910, Written Opinion dated May 26, 2011", (dated May 26, 2011), 4 pgs.
"International Application Serial No. PCT/US2012/022370, International Preliminary Report on Patentability dated Jul. 30, 2013", (dated Jul. 30, 2018), 6 pgs.
"International Application Serial No. PCT/US2012/022370, International Search Report dated May 25, 2012", (dated May 25, 2018), 2 pgs.
"International Application Serial No. PCT/US2012/022370, Written Opinion dated May 25, 2012", (dated May 25, 2012), 5 pgs.
"International Application Serial No. PCT/US2013/060983, International Preliminary Report on Patentability dated Mar. 24, 2015", (dated Mar. 24, 2015), 7 pgs.
"International Application Serial No. PCT/US2013/060983, International Search Report dated Mar. 27, 2014", (dated Mar. 27, 2018), 3 pgs.
"International Application Serial No. PCT/US2013/060983, Written Opinion dated Mar. 21, 2015", (dated Mar. 21, 2015), 6 pgs.
"International Application Serial No. PCT/US2015/010268, International Preliminary Report on Patentability dated Jul. 12, 2016", (dated Jul. 12, 2016), 5 pgs.
"International Application Serial No. PCT/US2015/010268, International Search Report dated Jul. 16, 2015", (dated Jul. 16, 2015), 2 pgs.
"International Application Serial No. PCT/US2015/010268, Written Opinion dated Jul. 16, 2015", (dated Jul. 16, 2015), 4 pgs.
"International Application Serial No. PCT/US2016/040286, International Preliminary Report on Patentability dated Jan. 2, 2018", (dated Jan. 2, 2018), 7 pgs.
"International Application Serial No. PCT/US2016/040286, International Search Report dated Jan. 5, 2017", (dated Jan. 5, 2017), 4 pgs.
"International Application Serial No. PCT/US2016/040286, Written Opinion dated Jan. 5, 2017", (dated Jan. 5, 2017), 6 pgs.
"Lighting for Layers", TAS Issue 17/05/2005, Technical Advice Sheet, (c) British United Turkeys Limited, (2005), 3 pgs.
"Machine Translation of 1st Office Action dated Aug. 9, 2016 for JP Application No. JP5195838", (dated Aug. 9, 2018), 3 pgs.
"Machine Translation of 1st Office Action dated Mar. 26, 2014 for JP Application No. JP2012524901", (dated Mar. 26, 2014), 2 pgs.
"Machine Translation of 1st Office Action dated Mar. 4, 2014 for JP Application No. JP2012524899", (dated Mar. 4, 2014), 3 pgs.
"Machine Translation of 1st Office Action dated Nov. 17, 2015 for JP Application No. JP2014261766", (dated Nov. 17, 2015), 4 pgs.
"Machine Translation of 2nd Office Action dated Dec. 19, 2014 for JP Application No. JP2012524901", (dated Dec. 19, 2014), 2 pgs.
"Natura 60", Big Dutchman The modern aviary for bard and free range egg production, (Apr. 2010), 3 pgs.
"Natura 70", Big Dutchman The modern aviary for bard and free range egg production, (Dec. 2010), 3 pgs.
"Sequential Linear LED Driver", Supertex inc. : DOC.# DSFP-CL8800, (2014), 7 pgs.
"TPS92411x Floating Switch for Offline AC Linear Direct Drive of LEDs with Low Ripple Current", Texas Instruments: SLUSBQ6B, (Oct. 2013), 29 pgs.
Bowmaker, James K. et al., "Evolution of vertebrate visual pigments", Current Biology vol. 16 No. 13 R484, (6 pgs).
Bruininx, E.M A. M., et al., "A prolonged photoperiod improves feed intake and energy metabolism of weanling pigs", Journal of Animal Science 80, (2002), 1736-1745.
Cao, J., et al., "Green and Blue Monochromatic Lights Promote Growth and Development of Broilers Via Stimulating Testosterone Secretion and Myofiber Growth", J. Appl. Poult. Res., 17(2), (2008), 211-218.
Carroll, Joseph, et al., "Photopigment basis for dichromatic color vision in the horse", Journal of Vision 1, (2001), 80-87.
Chiao, Chuan-Chin, et al., "Spectral tuning of dichromats to natural scenes", Vision Research 40, (2000), 3257-3271.
Clarke, S, et al., "Energy Efficient Swine Lighting", Ontario Ministry of Agriculture Food and Rural Affairs, (Jan. 2006), 8 pgs.
Claus, R, et al., "Influence of light and photoperiodicity on pig prolificacy", J Reprod. Fert., Supple 33, (1985), 185-197.
Dartnall, H. J.A, et al., "Human Visual Pigments: Microspectrophotometric Results from the Eyes of Seven Persons", Proceedings of the Royal Society of London. Series B, Biological Sciences 220(1218), (Nov. 22, 1983), 115-130.
Davis, N. J, et al., "Preferences of Growing Fowls for Different Light Intensities in Relation to Age, Strain and Behaviour", Animal Welfare 8(3), (199), 193-203.
El Halawani, M. E., et al., "Light Intensity Requirement for Breeder Hen Turkeys", Minnesota Turkey Gobbles, 66(4), (Jun. 2009), 3 pgs.
El Halawani, M. E., "Light spectrum and breeder hen turkeys egg production", Proeedings of the "Midwest Poultry Federation Convention", St. Paul., MN, (Oct. 2, 2007), 2 pgs.
Er, D., et al., "Effect of Monochromatic Light on the Egg Quality of Laying Hens", J. Appl. Poult, Res., 16(4), (2007), 605-612.
Gustafsson, G, et al., "Laying hens reactions on artificial light in a floor housing system", Agric Eng Int: CIGR Journal vol. 12, No. 2, (Jun. 2010), 21-30.
Halevy, O, et al., "Muscle development—Could environmental manipulations during embryogenesis of broilers change it?", 7 pgs.
Ham, A. D., et al., "Colour preferences and colour vision in poultry chicks", Proc. R. Soc. B, 274(1621), (2007), 1941-1948.
Jacobs, Gerald H, "Evolution of colour vision in mammals", Philosophical Transactions of the Royal Society 364, (2009), 2957-2967.

(56) References Cited

OTHER PUBLICATIONS

Jacobs, Gerald H, et al., "Photopigment basis for dichromatic color vision in cows, goats, and sheep", Visual Neuroscience 15, (1998), 581-584.
Kennedy, Donald, et al., "Selective Light Absorption by the Lenses of Lower Vertebrates, and Its Influence O N Spectral Sensitivity", The Biological Laboratories, Harvard University; Marine Biological Laboratory; and U. S. Fish and Wildlife Service Laboratory, Woods Hole, Mass., (1956), 12 pgs.
Kuhlmann, Josef, "Aviary System Layer Aviary", Farmer Automatic GmbH & CoKG, 4 pgs.
Kuhlmann, Josef, "Combi System Combi Layer System", Farmer Automatic GmbH & CoKG, 4 pgs.
Kuhlmann, Josef, "Floor System Layer Floor System", Farmer Automatic GmbH & CoKG, 4 pgs.
Kuhlmann, Josef, "Multi Deck System Layer Cage", Farmer Automatic GmbH & CoKG, 4 pgs.
Manci, William E, et al., "Design and Performance of an Electronic Lighting-Control Circuit That Simulates Sunrise and Sunset", The Progressive Fish-Culturist 54, (1992), 127-129.
Neitz, Jay, et al., "Spectral sensitivity of cones in an ungulate", Visual Neuroscience 2, (1989), 97-100.
Olanrewaju, H A, et al,, "A Review of Lighting Programs for Broiler Production", International Journal of Poultry Science 5 (4), (2006), 301-308.
Prayitno, D S, et al., "The Effects of Color and Intensity of Light on Behavior and Leg Disorders in Broiler Chickens", Poultry Science 76, (1997), 1674-1681.
Prescott, N. B., et al., "Spectral sensitivity of the domestic fowl (*Gallus g. domesticus*)", British Poultry Science, 40(3), (1999), 332-339.
Rahimi, G., et al., "The Effect of Intermittent Lighting Schedule on Broiler Performance", International Journal of Poultry Science, 4(6), (2005), 396-398.
Rozenboim, I, et al., "New Monochromatic Light Source for Laying Hens", Poultry Science, 77, (1998), 1695-1698.
Rozenboim, I., et al., "The effect of a green and blue monochromatic light combination on broiler growth and development", Poultry Science, 83(5), (2004), 842-845.
Rozenboim, I., et al., "The Effect of Monochromatic Light on Broiler Growth and Development", Poultry Science, 78(1), (1999), 135-138.
Taylor, Todd, "Great Green Hope: The Corporate Love Affair With Algae", Biomass Magazine, (Apr. 2010), 2 pgs.
Wilson, M., et al., "Impact of Lighting Programs on Broiler Performance", Technical Focus, vol. 1, No. 1, (c) 2011 COBB South Affrica, (2011), 4 pgs.
Woodard, A E, et al., "Effect of Wave Length of Light on Growth and reproduction in Japanese Quail", Oxford Journals.org, (Jun. 4, 1968), 6 pgs.
"U.S. Appl. No. 14/906,685, Appeal Brief filed Oct. 5, 2017", 16 pgs.
"U.S. Appl. No. 14/906,685, Examiner Interview Summary dated Feb. 14, 2018", 3 pgs.
"U.S. Appl. No. 14/906,685, Final Office Action dated Dec. 5, 2016", 8 pgs.
"U.S. Appl. No. 14/906,685, Non Final Office Action dated Jun. 14, 2016", 9 pgs.
"U.S. Appl. No. 14/906,685, Non Final Office Action dated Nov. 9, 2017", 8 pgs.
"U.S. Appl. No. 14/906,685, Notice of Allowance dated Mar. 9, 2018", 7 pgs.
"U.S. Appl. No. 14/906,685, Preliminary Amendment filed Jan. 21, 2016", 3 pgs.
"U.S. Appl. No. 14/906,685, Response filed Nov. 11, 2016 to Non Final Office Action dated Jun. 14, 2016", 7 pgs.
"U.S. Appl. No. 14/906,685 Response filed Feb. 8, 2018 to Non-Final Office Action dated Nov. 9, 2017.pdf", 6 pgs.
"Chinese Application Serial No. 201480047295.6, First Office Action dated Apr. 24, 2017.", w. English Translation, 12 pgs.
"Chinese Application Serial No. 201480047295.6, Second Office Action dated Sep. 26, 2017", w. English Translation, 11 pgs.
"European Application Serial No. 15734927.5, search report dated May 9, 2017", 8 pgs.
"International Application Serial No. PCT/US2014/049143, International Preliminary Report on Patentability dated Feb. 11, 2016", 6 pgs.
"International Application Serial No. PCT/US2014/049143, International Search Report dated Nov. 6, 2014", 2 pgs.
"International Application Serial No. PCT/US2014/049143, Written Opinion dated Nov. 6, 2014", 4 pgs.
"International Application Serial No. PCT/US2015/010407, International Preliminary Report on Patentability dated Jul. 21, 2016", 6 pgs.
"International Application Serial No. PCT/US2015/046641, International Preliminary Report on Patentabililty dated Mar. 9, 2017.", 7 pgs.
"International Application Serial No. PCT/US2015/046641, Search Report Written Opinion dated Nov. 24, 2015.", 8 pgs.
"International Application Serial No. PCT/US2017/024679, International Search Report dated Aug. 2, 2017", 4 pgs.
"International Application Serial No. PCT/US2017/024679, Invitation to Pay Additional Fees and Partial Search Report dated Jun. 7, 2017", 2 pgs.
"International Application Serial No. PCT/US2017/024679, Written Opinion dated Aug. 2, 2017", 5 pgs.
Claus, R, et al., "Influence of light and photoperiodicity on pig prolificacy", Journals of Reproduction & Fertility Ltd. (1985), 185-197.

* cited by examiner

SYSTEM AND METHOD OF ENHANCING SWINE REPRODUCTION

CROSS-REFERENCE TO RELATED APPLICATIONS

This application is a U.S. National Stage Application under 35 U.S.C. 371 from International Application No. PCT/US2015/010407, filed Jan. 7, 2015, which application claims the benefit of priority to U.S. Provisional Patent Application entitled "System and Method of Enhancing Swine Reproduction," Ser. No. 61/924,477, filed on Jan. 07, 2014, the entire contents of which are incorporated herein by reference.

BACKGROUND

This invention relates to swine reproduction. More specifically this invention relates to stimulating, facilitating and enhancing the swine breeding using a LED lighting system.

Farmed animal reproduction has grown into a multi-million dollar business. For years, in the horse racing field, racing champions have been selected to stud mares in hopes of providing an offspring that will similarly be a champion racer.

In the swine industry the breeding of swine has become its own industry. In particular, as the swine industry has become more modernized not only have the swine moved indoor to confinement facilities, a greater emphasis on efficiency within swine operations has been emphasized. This is true among all facets of swine production including reproduction.

In an effort to increase efficiencies within the swine facility regarding reproduction, artificial insemination has become a common method to support breeding within swine facilities. The process of artificial insemination has multiple benefits within the swine industry. First, this allows humans to be able to monitor for estrous female swine and ensure delivery of boar semen at the optimal time for conception, thus increasing the likelihood of successful impregnation. Second, because there is human delivery of the semen, exact record keeping of the breeding process can be documented. This allows for more accurate mating information as well as gestation and litter data. Finally, as part of the artificial insemination process, the sperm of the boar can be selected depending on the type of piglet desired.

While these advantages of the artificial insemination process exist, problems remain. In particular, the artificial insemination process is expensive. Thus, ensuring that when the process in undertaken that the female swine become impregnated is paramount to the process. This remains problematic for multiple reasons. First, female swine ovulate at different times from one another, causing the need for constant monitoring and potential missed cycles. In addition, research has shown that female swine are most fertile during winter months and conversely demonstrate a tendency towards reduced conception during summer months. Also, not all boar ejaculate is optimal for breeding. In particular, sperm concentration and motility vary from boar to boar. In consequence, boars and boar semen for artificial insemination are sold with increased prices for the best boar or boar semen for conception. In particular, high performance boars are auctioned off for premier prices.

Thus, a need in the art exists to facilitate successful breeding of swine. In particular, increased chances of successful breeding during all times of the year are desired along with maximizing the chances of conception using the artificial insemination method of reproduction.

SUMMARY OF THE INVENTION

A method of increasing the probability of breeding swine via a lighting system with a programmable timing device. The lighting system is programmed to present predetermined periods of light and dark for the swine every twenty four hours for a first pre-determined amount of time, typically a week. During this period the dark light is mere dark light for the swine, which can include red wavelength light. After the first pre-determined amount of time the predetermined periods of light and dark changed such that the amount of dark time increases and light time decreases over a second predetermined period of time, such as another week. Then this occurs again, over a third predetermined period of time such that the swine believes lighting is going from summer into fall or between predetermined season, causing an increase in the probability of breeding for the swine.

Thus a principle object of the present invention is to enhance breeding in animals using light. Another object of the present invention is to provide a systematic easily reproducible method of enhancing breeding in animals. These and other objects, advantages and improvements will be apparent from the rest of the specification and claims.

DETAILED DESCRIPTION

Figure 1:
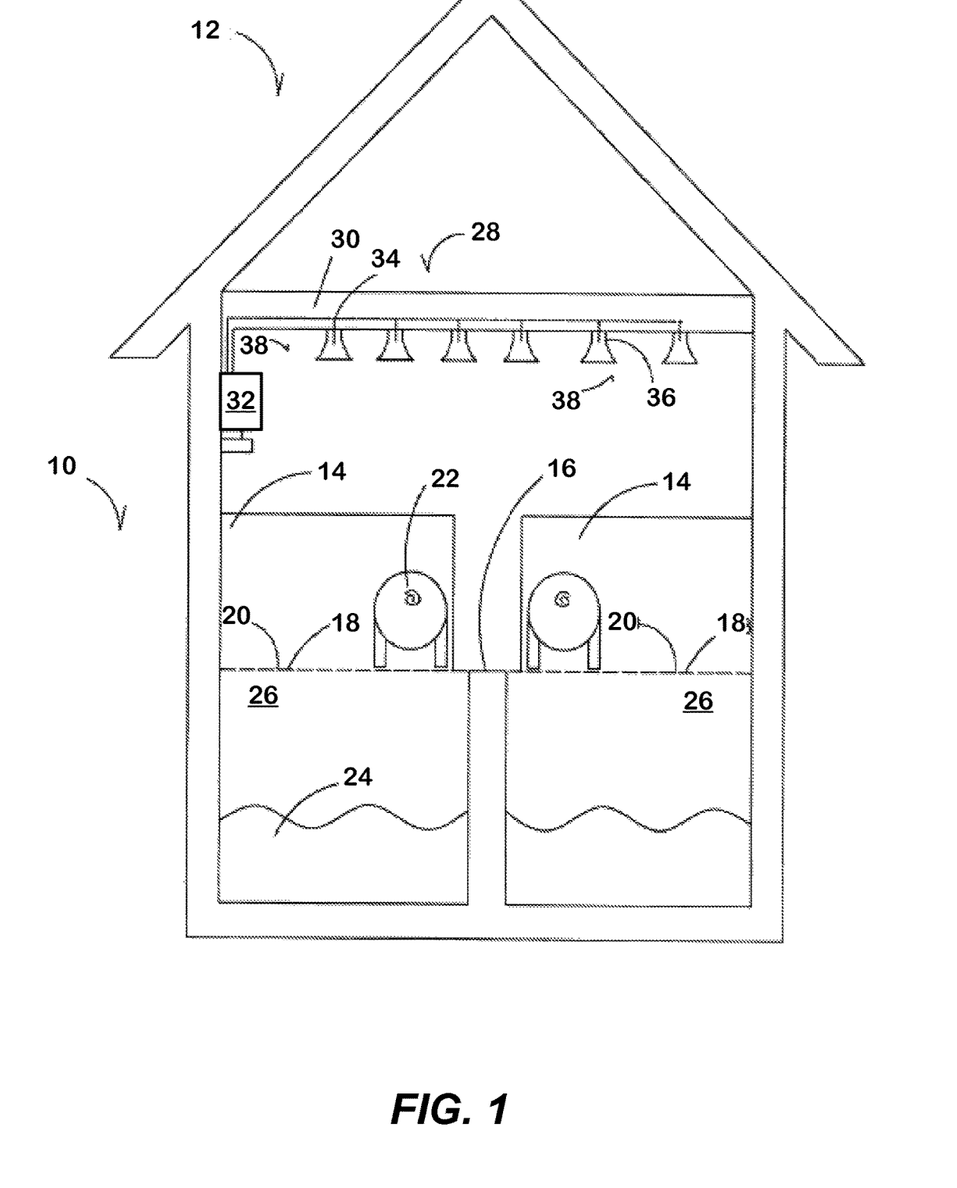
FIG. 1 is a side plan view of an animal confinement facility.

The figures show an animal confinement facility 10 that in a preferred embodiment is a facility 10 that confines swine. Still, other animals, including horses, avian, bovine, and other domesticated animals such as sheep and goats, aquatic life including fish and shrimp, or the like could be within the facility without falling outside the scope of this disclosure. In this preferred embodiment the facility 10 is directed toward a swine confinement facility 10, but again could be any such different facility 10.

The figures show the swine facility 10 that includes a dwelling 12 such as a barn or hog containment facility. The dwelling 12 has a plurality of containment units 14 such as pens, stalls and the like. The floor 16 of the containment units 14 consist of a plurality of slat elements 18 that sit in paralleled spaced relation to one another to form a plurality of openings 20 between consecutive slat elements 18. In one embodiment the slat elements 18 are angled or slanted with one end higher than the other to cause a downward slope toward an opening 20 in the floor 16. In this manner when a swine 22 steps on or rolls on feces the feces is pushed through the openings 20 below the floor 16. Similarly, during wash down of the containment units 14 the feces is power sprayed and the water and feces 24 go through the openings 20 beneath the floor and into a reservoir 26.

The figure also shows a lighting system 28 that in one embodiment includes a plurality of electrical conduit bodies 30 that receive and electrical input from an electrical source 32. The lighting system is of any type, including but not limited to those as previously described in U.S. Pat. No. 8,596,804 entitled Light Sources Adapted to Spectral Sensitivity of Diurnal Avians and Humans, U.S. Ser. No. 12/916,313 entitled LED Lighting for Livestock Development, U.S. Prov. Pat. App. 61/861,645 entitled System and Method for Manipulating Psychological and Physiological Characteristics of Swine, all to Grajcar and all of which are fully incorporated by reference herein. The electrical conduit bodies 30 house wiring 34 that extend to provide an electric excitation signal to different areas in the dwelling. In one embodiment the wiring is electrically connected to a socket 36 to receive a lighting assembly 38.

Figure 2:
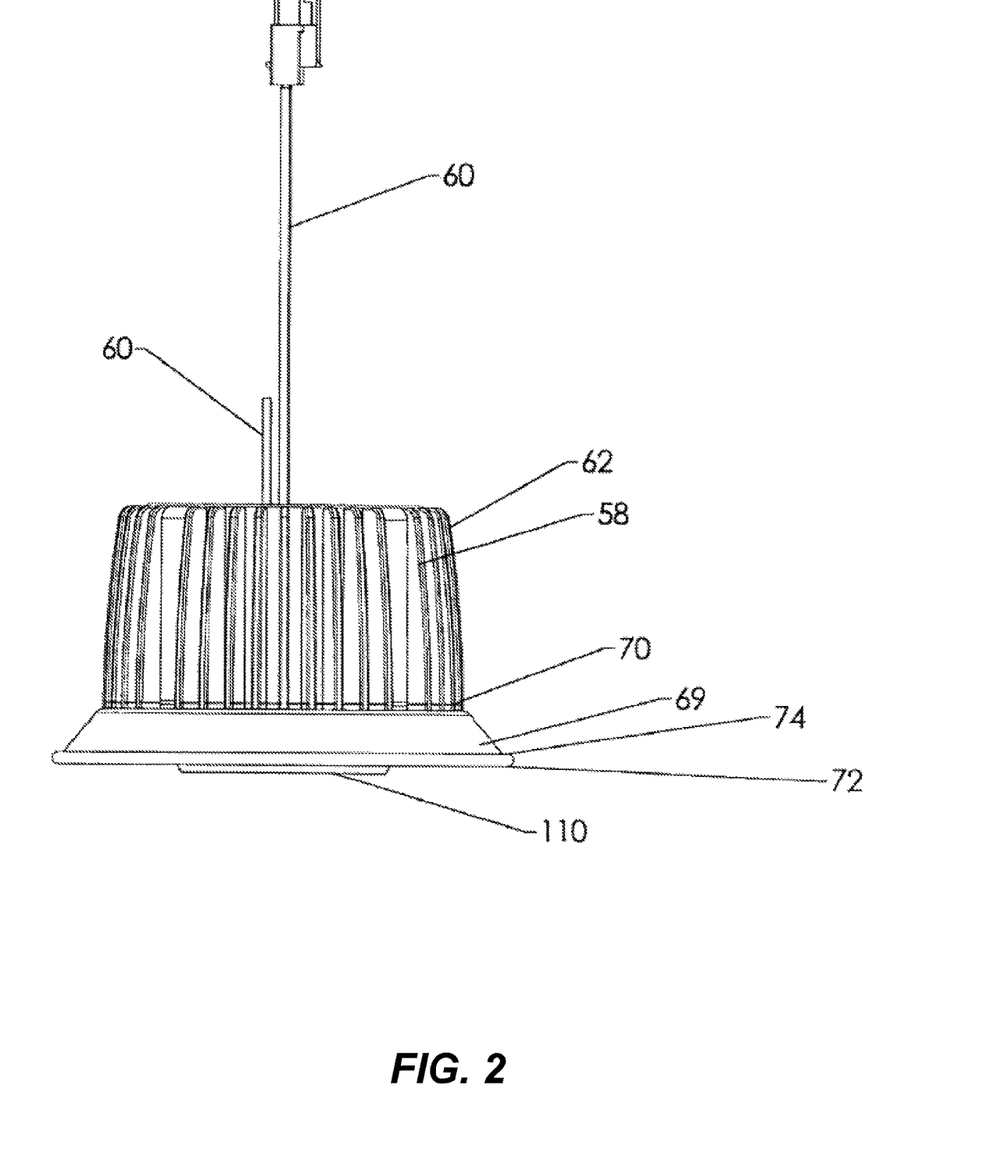
FIG. 2 is a side plan view of a lighting device of a lighting system.
Figure 3:
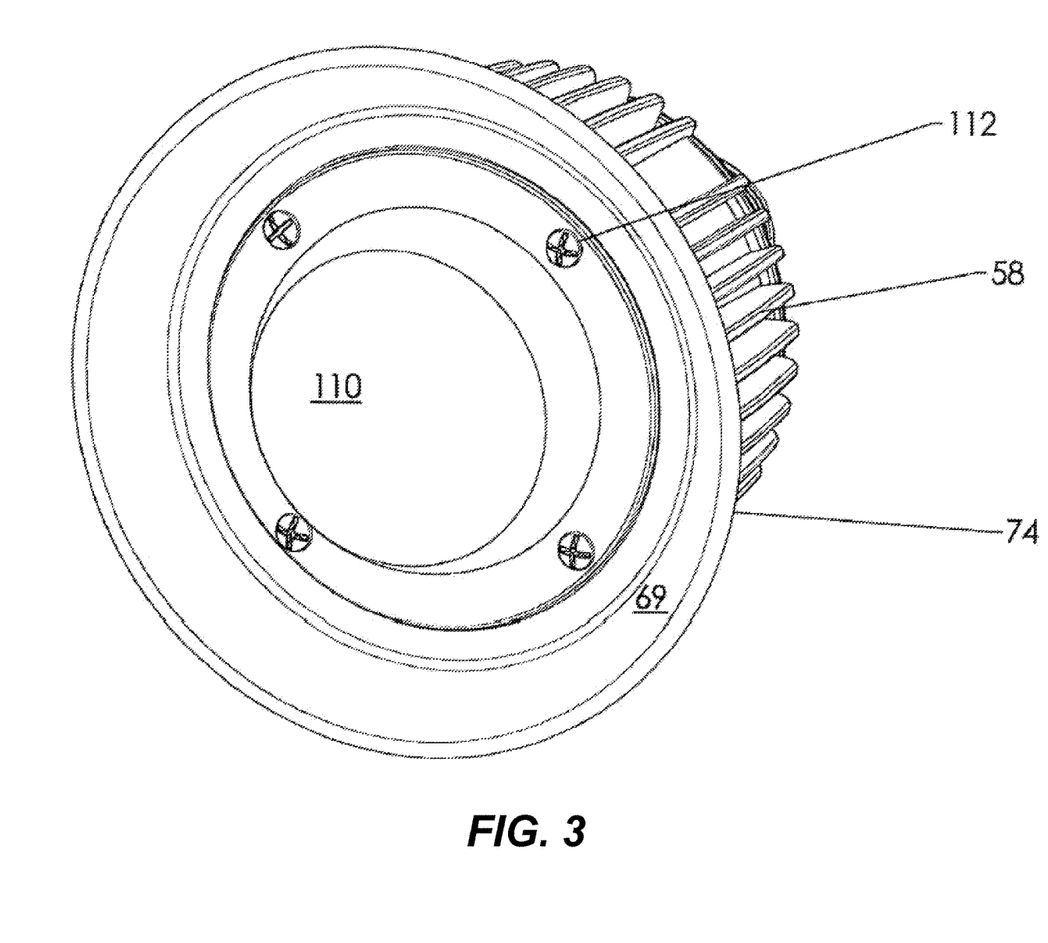
FIG. 3 is a side perspective view of a lighting device of a lighting system.
Figure 4:
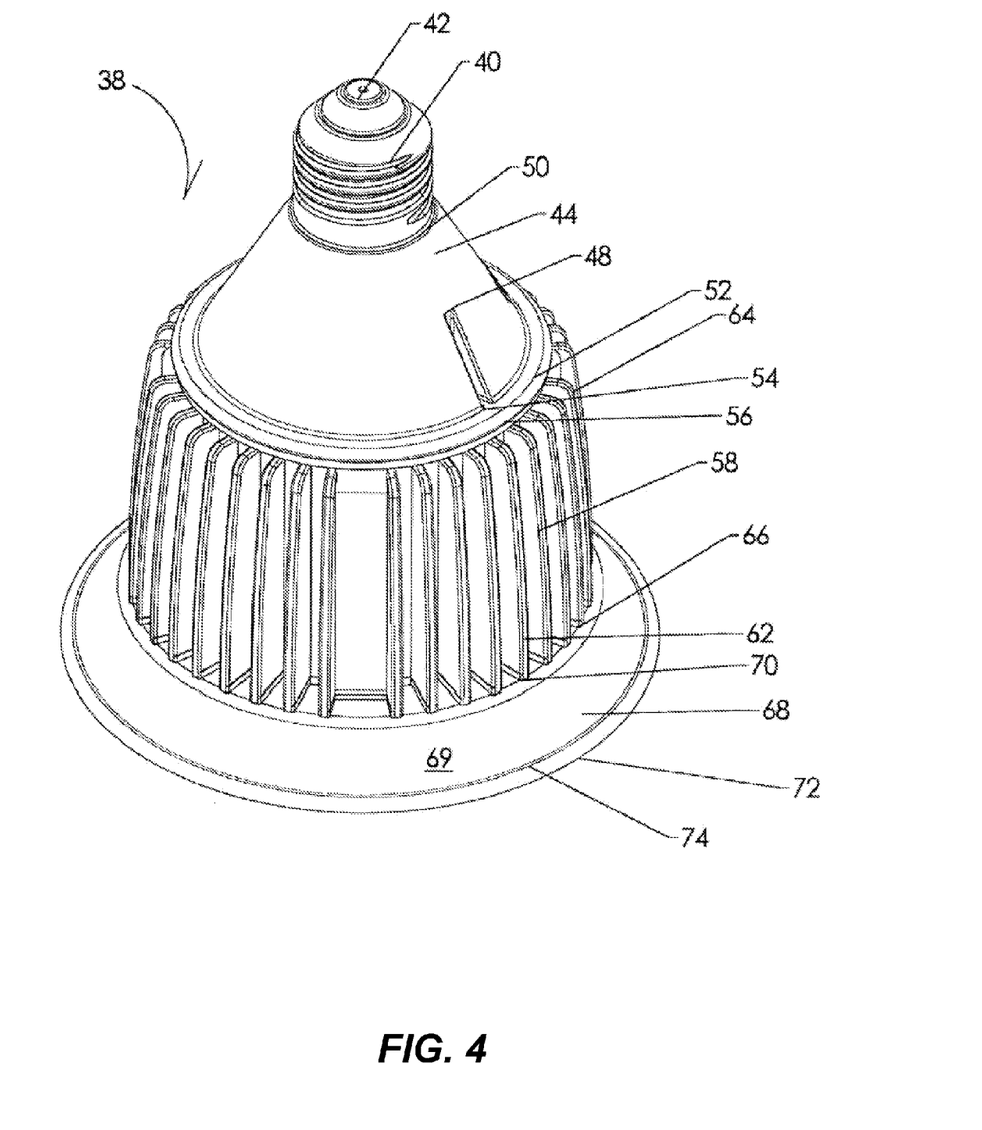
FIG. 4 is a top perspective view of a lighting device of a lighting system.

The lighting assembly 38 includes a base 40 having electrical conducting elements 42 therein that threadably and electrically connects within the socket 36 as is known in the art. The base 40 is either threadably received or compression fit onto a frustroconally shaped body 44 having a hollow interior 46 and a sidewall 48 that extends outwardly and away from a first end 50 having a first diameter to a second end 52 having a second diameter greater than the first diameter. In this manner when waste or feces or water is sprayed on the body 44 the material flows downwardly and off the assembly 38. At the second end is a ring element 54 that is of size and shape to engage a sealing element 56 that in a preferred embodiment is made from an elastic material that expands upon compression. The sealing element 56 is secured between the ring element 54 and heat sink 58 to provide a water tight seal there between. In this manner electrical wiring 60 is electrically connected to the conductive body through the body 44 and heat sink within a water tight assembly 38.

In an alternative embodiment a socket 36 is not presented and instead the wiring is directly provided. In this embodiment the body 44 with the base 40 are not provided and instead the electrical wiring 60 disposed through the heat sink 58 is directly or hard wired to the wiring 34 of the conduit to provide a direct electrical connection. The heat sink 58 is then threadably and/or sealing connected to the conduit again to provide a water tight seal to prevent water from being within the interior of the heat sink 58 and being exposed to the electrical wiring 60.

The heat sink 58 in a preferred embodiment is made of a plastic material and has a plurality of fin elements 62 that assist in conveying heat through the sink 58. The heat sink 58 extends from a first end 64 adjacent the conduit bodies 30 that receives the sealing element 56 in one embodiment and is sealed to a conduit body 30 in another to second end 66. The second end 66 is secured to a diffusion element 68 that has a frustroconical shape having a sidewall 69 that extends from a first end 70 outwardly and downwardly from the heat sink 58 to an open second end 72 having a diameter slightly greater than the diameter of the first end 70 and terminating in a lip element 74. By being sloped at an angle and downwardly, again, water, feces and other materials often known to swine facilities 10 flow off the diffusion element 68, yet the lip element 74 keeps a robust design to withstand the harsh environment.

Figure 6:
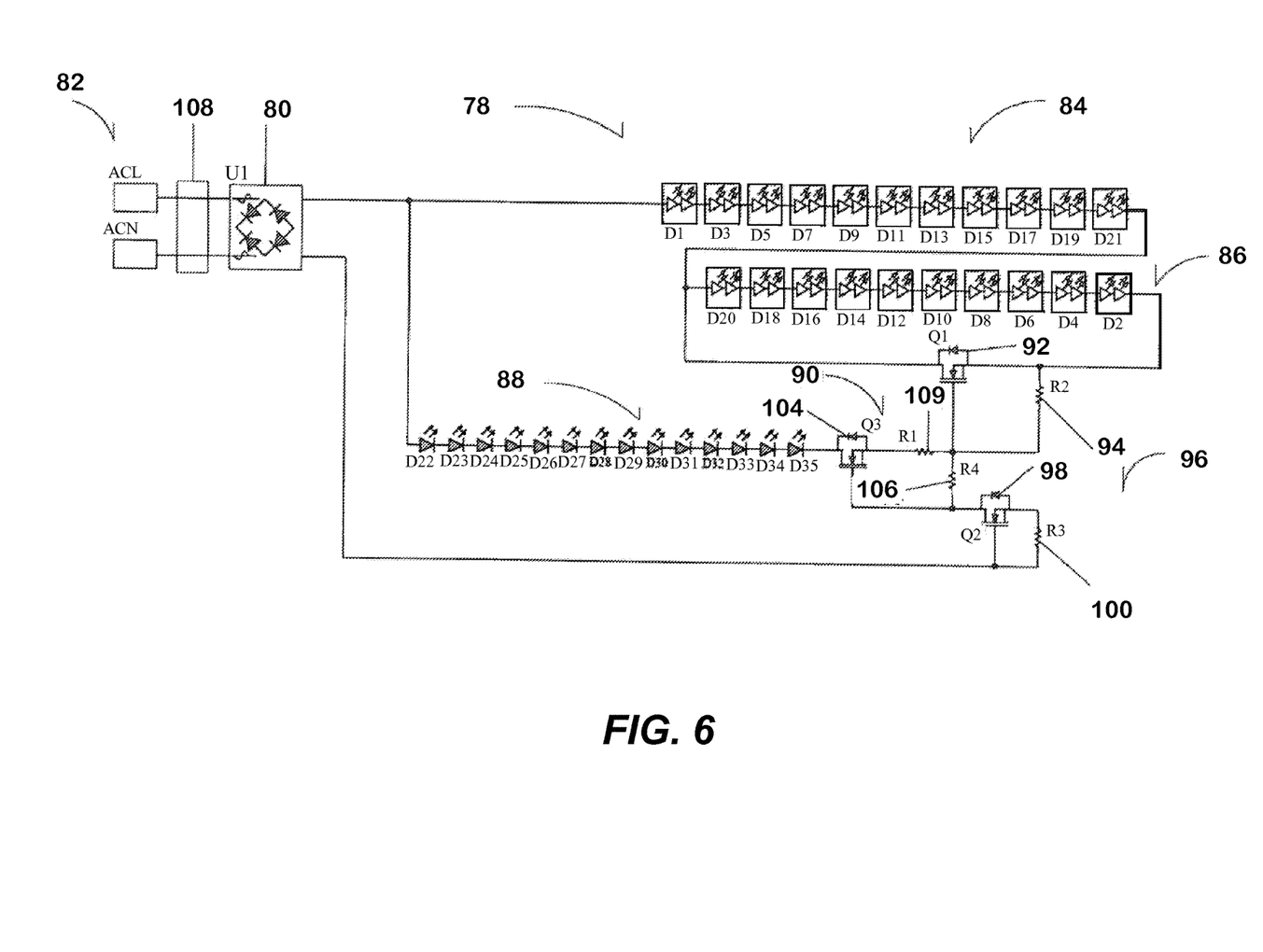
FIG. 6 is a schematic diagram of circuitry of a lighting system.

A substrate is also secured to the second end 66 of the heat sink 58 and in one embodiment has a generally round shape. The substrate also in one embodiment is a printed circuit board. The substrate includes driving circuitry 78, as shown in FIG. 6. The circuitry is similar to that taught in U.S. Pat. No. 8,373,363 entitled Reduction of Harmonic Distortion for LED Loads, by Z. Grajcar and issued on Feb. 12, 2013 and U.S. Patent Application entitled "Color Temperature Shift Control for Dimmable AC LED Lighting," Ser. No. 12/824,215, which was filed by Z. Grajcar on Jun. 27, 2010, the entire contents of each of which are incorporated herein by reference.

The circuitry 78 of the present invention includes a rectifying device 80 that receives current from an AC source 82 and includes a first group of light emitting diodes 84 arranged in series with a second group of light emitting diodes 86, both of which comprise diodes emitting white light. A third group of light emitting diodes 88 comprising diodes emitting red light are presented in parallel to the first and second groups of diodes 84 and 86. Red light emitted is considered any light having a wavelength approximately between 620 nm and 780 nm. Alternatively, light emitting diodes providing blue light, or having a wavelength approximately between 400 nm and 500 nm, could be used without falling outside the scope of this invention. A bypass path 90 is presented with a first impedance element 92 that in one embodiment is a transistor. In a preferred embodiment the first impedance element 92 is a depletion MOSFET, though a p-channel MOSFET, n-channel MOSFET or the like can be used without falling outside the scope of this disclosure, even if an additional transistor is required for functionality purposes. A first resistor 94 is also provided to control the flow of current through the first impedance element 92 to provide smooth and continuous current flow.

A second bypass path 96 is also provided with a second impedance element 98 that similarly in one embodiment is a depletion MOSFET. Similar to the first bypass path 90 the second bypass path 96 utilizes a second resistor 100 again to control the impedance element 98. Similarly also, a third bypass path 102 is provided between the third group of light emitting diodes 88 and first and second groups of light emitting diodes 84 and 86. Again, this bypass path 102 utilizes a third impedance element 104 and third resistor 106 to provide similar functionality as the other bypass paths. In this manner when a dimming device 108 is electrically connected to the circuit and the voltage begins dropping, current flow to the first group of diodes 84 drops first, dimming out the first group of white diodes. Then as dimming continues and a threshold current is reached the second group of light emitting diodes 86 begin to dim. Thus, again white light is slowly dimmed and eliminated from the output light. In this manner only the third group of light emitting diodes 88 that are red remain providing light. A supplemental resistor 109 optionally is provided to limit current in the system and to improve efficiencies.

Therefore the assembly dims to produce a red light. Consequently, with a programmable dimming device the lighting assembly 38 can provide a combination of white and red light throughout a 24 hour period to optimize swine characteristics.

A lens element 110 is secured to the heat sink 58, diffusion element 68 or both. In one embodiment fastening elements 112 are utilized to provide the connection. In particular the lens element 110 is secured to provide a water tight seal so that water cannot encroach the interior of the assembly 38.

Figure 5:
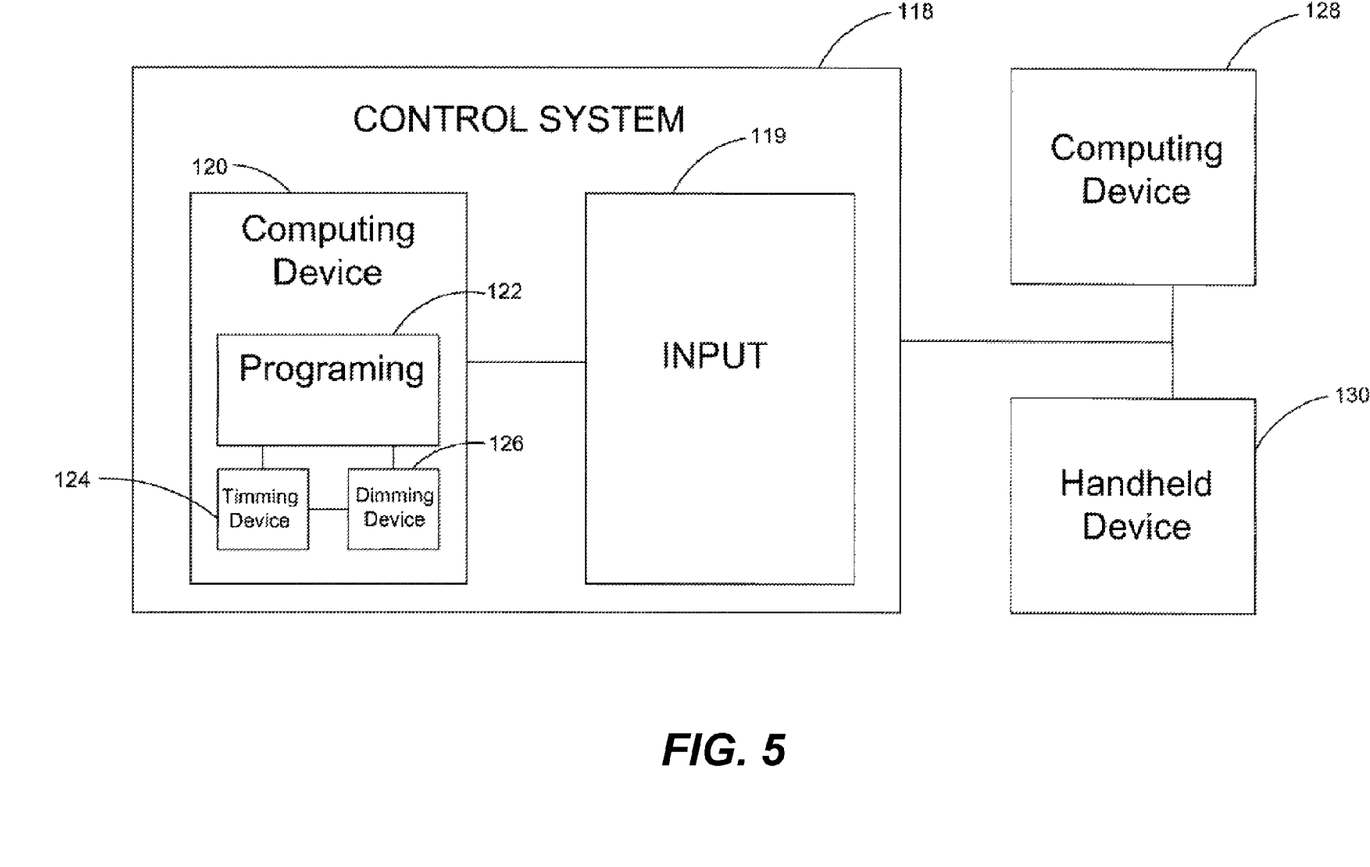
FIG. 5 is a schematic diagram of a control system for a lighting system.

A control system 118 is electronically connected to the lighting assemblies 38. The control system 118 includes an input 119 for actuating a computing system 120 having programming 122 therein associated with a timing device 124. The control system 118 additionally has a dimming device 126 that is electrically connected to the timing device 124 such that the programming 122 at predetermined periods will automatically dim the lighting assemblies 38 to a predetermined light setting. The control system 118 in one embodiment communicates remotely through over the air communications, via Wi-Fi or as is known in the art to provide lighting and dimming information to an individual having a remote computing device 128 or handheld device 130 having the capability to receive such communication. In one embodiment the computing device 128 or handheld device 130 may be used to communicate instructions to the control system 118 such that the control system 118 is remotely controlled by the remote device 128 or 130. Examples of the remote devices include but are not limited to computers, laptop computers, tablets, Ipads, smartphones, blackberries, remote controls and the like.

The lighting assemblies 38 are designed as described above such that the light includes different wavelengths or colors. In this manner a dimming device 126 when actuated will change the color of the lighting assembly from a first predetermined color to a second predetermined color. In one embodiment the first predetermined color is white and as the lighting assemblies are dimmed down the light output becomes red. In another embodiment the first predetermined color is white and the second predetermined color is blue. In yet another embodiment the first predetermined color is red and the second predetermined color is blue.

The lighting assemblies 38 are also spread out evenly across the facility 10, in one embodiment in a grid like manner, such that a generally evenly spread out intensity of light is provided on the swine. In this manner no change in light intensity is detected by the swine 22 providing a calming condition to the swine 22. Thus stress on the swine 22 is reduced providing a healthier swine 22 that is less susceptible to diseases such as ulcers.

Thus, in operation the control system 118 is programmed to provide not only predetermined wavelengths or colors, in addition the timing device 124 sets predetermined intervals for each day. In particular, the control system 118 can provide 16 hours of white light during a day and then actuate the dimming device 126 to dim the lighting assemblies 38 to a red light for eight hours. Then after the eight hours, the dimming device 126 is actuated to again provide white light. The programming 122 can additionally be configured to then vary the predetermined durations of time. Thus, for a first time period, such as a day or week the control system 118 provides a predetermined interval of 16 hours of white light and eight hours of red light. Then for a second time period, such as a next day or week, the predetermined interval can go to a different predetermined time interval, such as fourteen hours of white light and ten hours of red light. Then during a third time period the predetermined time intervals can be changed to provide twelve hours of white light and twelve hours of red, and so on, such that any predetermined levels can be accomplished by the lighting assemblies 14 in a given day. Thus any daily photoperiod and light spectrum desired by an end user can be provided.

In one embodiment the control system 118 is used on lighting assemblies 38 that are actuated to provide fourteen hours of white light for the swine and ten hours of red light which is provided for a first week. Then every week the control system 118 reduces the amount of white light and increases the amount of red light by an hour, such that in the second week thirteen hours of white light is provided and eleven hours of red light, in week three 12 hours of white light and twelve hours of red light, in week four 11 hours of white light and thirteen hours of red light, in week five 10 hours of white light and fourteen hours of red light, in week six 9 hours of white light and fifteen hours of red light, and finally in week seven 8 hours of white light and sixteen hours of red light.

Then, in this preferred embodiment in week eight, every day the white light, red light predetermined periods are reversed back, such that on a first day nine hours of white light is presented and fifteen hours of red light, on the second day ten hours of white light and fourteen hours of red light and so on until fourteen hours of white light and ten hours of red light is again provided. At this point again the control system steps down the amount of white light one week at a time such that in week nine 14 hours of white light and ten hours of red light is provided, in week ten 13 hours of white light and eleven hours of red light is provided, in week eleven 12 hours of white light and twelve hours of red light are provided, and so on until again eight hours of white light is presented with sixteen hours of red light.

In this embodiment, because swine do not perceive red light, the red light is considered a dark period for the swine even though humans are still able to see within the confinement facility 10. As a result of decreasing the photoperiod over a seven week period swine are cued to a fall/winter seasonality, which in nature results in the female swine being at their most fertile condition and male swine producing there highest concentration of seamen.

In addition to increasing predictability and optimizing artificial insemination for the female swine, the male swine sperm is simultaneously enhanced as a result of the use of the red wavelength of light. In particular, every mammalian sperm, and fish contains one or more mitochondrion located between flagellar primordium (flagellum) and sperm nucleus. Mitochondrial energy levels as indicated by the amount of the adenosine triphosphate (ATP) within the mitochondria determine flagellar beating frequency and also time of beating, or motility.

Cytochrome C Oxidase is a photosensitive protein that is one of the four protein complexes in the outer mitochondria membrane. Specifically, cells in a redox (reduction-oxidation) state are more sensitive to light than those in a normal state and the voltage potential between the inner and outer mitochondrial membrane changes under photostimulation by far-red and infrared (IR) light. This change in voltage potential between the inner and outer mitochondrial membrane thus triggers ATP production. Specifically, Cytochrome C Oxidase has a copper core and the rest of four protein complexes involved in outer shell of the mitochondrion also contain metals.

Due to the redox state, there are a lot of ions present that is very similar to a photovoltaic cell. Therefore, by providing an external light source of right spectrum and frequency to mitochondria ATP, production is enhanced increasing sperm motility.

In one embodiment the spectrum is in the red spectrum of light or 620 nm-750 nm. In another embodiment the spectrum is more than 750 nm and in other embodiments the spectrum is less than 620 nm. Still, by selecting a predetermined spectrum, ATP production is enhanced and sperm motility enhanced, thus increasing conception for swine as compared to a similarly situated swine had no light treatment been provided. In one embodiment the spectrum is provided by supplemental lighting used during the artificial insemination process to increase motility a predetermined amount of time, such as within one hour, of delivery to the semen to the female swine. Therefore success in breeding in again enhanced.

In yet another embodiment flagellar beating is caused by voltage differential pulses caused by pulsed light. In this manner flagellar beating is caused directly by the pulsing light, again increasing motility and thus increasing the probability of breeding as compared to rates had no light treatment been provided.

Thus provided is a system and method that increases predictability and probability of breeding of swine as compared to the predictability and probability of breeding without use of the system and method. In particular a lighting regime and system provides periodic decreases in light over a period thus causing male and female swine to perceive that a winter photoperiod is presented, providing higher probability of conception, but in addition, providing a cycle for the swine so that the time of conception becomes more predictable and better data can be provided. Further, by evenly distributing light, a calmer healthier swine is provided.

In addition, by using a predetermined wavelength of light, and in one embodiment in the 620 nm-750 nm range, physiologically the sperm quality for male swine is also increased. In this manner the probability of successful breeding of swine as compared to the probability of successful breeding without use of the system and method is increased. Therefore, all of the stated problems are overcome.

What is claimed:

1. A method of increasing the probability of breeding swine, steps comprising:
   providing a lighting system having a programmable timing device;
   providing with the lighting system predetermined periods of light and dark for the swine every twenty four hours for a first pre-determined amount of time;
   after the first pre-determined amount of time providing predetermined periods of light and dark for the swine every twenty four hours during a second pre-determined amount of time;
   wherein the predetermined periods of light and dark for the swine during the second pre-determined amount of time comprises a greater amount of dark for the swine and less light than the first pre-determined amount of time;
   after the second pre-determined amount of time providing predetermined periods of light and dark for the swine every twenty four hours during a third pre-determined amount of time;
   wherein the predetermined periods of light and dark for the swine during the third pre-determined amount of time comprises a greater amount of dark for the swine and less light than the second pre-determined amount of time to increase the probability of breeding swine.

2. The method of claim 1 wherein the pre-determined periods of light and dark during the first pre-determined amount of time is 16 hours of light and 8 hours of dark and the pre-determined periods of light and dark during the third pre-determined amount of time is 8 hours of light and 16 hours of dark.

3. The method of claim 1 wherein the period of dark for the swine is provided by a wavelength of light of between 620 nm-750 nm.

4. The method of claim 1 wherein the first pre-determined amount of time is one week.

5. The method of claim 1 wherein the second pre-determined amount of time is one week.

6. The method of claim 1 wherein the pre-determined periods of light and dark during the second predetermined amount of time includes fourteen hours of white light and ten hours of red light.

7. The method of claim 1 wherein the pre-determined periods of light and dark during the third predetermined amount of time includes twelve hours of white light and twelve hours of red light.

8. The method of claim 1 wherein the pre-determined period alight is reduced by one hour and the pre-determined period of dark is increased by one hour during the second pre-determined amount of time.

9. The method of claim 1 wherein the pre-determined periods of light and dark during the first pre-determined amount of time is fourteen hours of light and ten hours of dark and the pre-determined period of light is reduced by one hour and the pre-determined period of dark is increased by one hour during the second pre-determined amount of time.

10. The method of claim 1 wherein the first pre-determined amount of time is one week and the pre-determined period of light is reduced by one hour and the pre-determined period of dark is increased by one hour during the second pre-determined amount of time and each subsequent pre-determined one-week amount of time over the course of seven weeks.

11. The method of claim 10 wherein an eighth pre-determined amount of time is one week and the pre-determined period of light is increased by one hour and the pre-determined period of dark is decreased by one hour during a ninth pre-determined amount of time and each subsequent pre-determined one-week amount of time over the course of seven weeks.

12. The method of claim 1 further comprising:
   after the third pre-determined amount of time, providing predetermined periods of light and dark for the swine every twenty-four hours during a next predetermined amount of time;
   wherein the predetermined periods of light and dark for the swine during the next pre-determined amount of time comprises a greater amount of light for the swine and less dark than during the third predetermined amount of time.

* * * * *